(12) United States Patent
Larin et al.

(10) Patent No.: US 11,839,483 B2
(45) Date of Patent: Dec. 12, 2023

(54) EVALUATION OF DERMAL FILLER INJECTIONS BY OPTICAL COHERENCE TOMOGRAPHY AND OPTICAL COHERENCE ELASTOGRAPHY

(71) Applicant: University of Houston System, Houston, TX (US)

(72) Inventors: Kirill Larin, Friendswood, TX (US); Richard Yee, Houston, TX (US); Manmohan Singh, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 851 days.

(21) Appl. No.: 15/748,372

(22) PCT Filed: Aug. 25, 2016

(86) PCT No.: PCT/US2016/048636
§ 371 (c)(1),
(2) Date: Jan. 29, 2018

(87) PCT Pub. No.: WO2017/035328
PCT Pub. Date: Mar. 2, 2017

(65) Prior Publication Data
US 2018/0214069 A1    Aug. 2, 2018

Related U.S. Application Data

(60) Provisional application No. 62/210,195, filed on Aug. 26, 2015.

(51) Int. Cl.
*A61B 5/00* (2006.01)
*A61B 90/00* (2016.01)

(52) U.S. Cl.
CPC ............ *A61B 5/442* (2013.01); *A61B 5/0066* (2013.01); *A61B 5/4839* (2013.01);
(Continued)

(58) Field of Classification Search
CPC combination set(s) only.
See application file for complete search history.

(56) References Cited

U.S. PATENT DOCUMENTS

2005/0119568 A1* 6/2005 Salcudean ........... G01S 15/8977
600/437
2010/0160849 A1* 6/2010 Barbour ................. A61K 38/39
604/20

(Continued)

OTHER PUBLICATIONS

Twa MD, Li J, Vantipalli S, et al. Spatial characterization of corneal biomechanical properties with optical coherence elastography after UV cross-linking. Biomedical Optics Express. May 2014;5(5):1419-1427. (Year: 2014).*

(Continued)

*Primary Examiner* — Nathan J Jenness
*Assistant Examiner* — Michael A Catina
(74) *Attorney, Agent, or Firm* — Jackson Walker LLP (57) ABSTRACT

Methods and systems for providing depth-resolved real-time visual feedback to a physician during cosmetic dermal filler injections with micrometer spatial resolution utilizing a noninvasive optical coherence tomography/elastography, 2D-3D virtual and real time system. This system can be automated to direct proper volumes and viscosity of the necessary injection substances. The methods and systems allow for assessment of the elasticity of the tissue before and after the injection to evaluate the efficacy of the injection, with predetermined virtual results before and matched post injection images. The elasticity assessment method preferably utilizes a focused air-pulse to induce a micrometer scale displacement in the skin and the optical coherence tomography system to image this displacement. By utilizing a model-based reconstruction method, the viscoelasticity of (Continued)

the tissue at a specific measurement position can be obtained and virtual and post injection real time projections can be imaged.

9 Claims, 10 Drawing Sheets

(52) U.S. Cl.
CPC .... *A61B 5/4848* (2013.01); *A61B 2090/3735* (2016.02); *A61B 2505/05* (2013.01)

(56) References Cited

U.S. PATENT DOCUMENTS

2015/0011895 A1* 1/2015 Johnstone ............ A61B 5/0051
600/476
2017/0328794 A1* 11/2017 McLaughlin ........... G01L 1/241

OTHER PUBLICATIONS

Notification of Transmittal of the International Preliminary Report on Patentability for PCT/US2016/048636 with the Written Opinion by the International Searching Authority—Korean Intellectual Property Office—as mailed by the International Bureau of WIPO dated Mar. 8, 2018, 7 pages.

* cited by examiner

EVALUATION OF DERMAL FILLER INJECTIONS BY OPTICAL COHERENCE TOMOGRAPHY AND OPTICAL COHERENCE ELASTOGRAPHY

This application claims priority to U.S. Provisional Patent Application Ser. No. 62/210,195 entitled "Evaluation of Dermal Filler Injections by Optical Coherence Tomography and Optical Coherence Elastography," filed on Aug. 26, 2015, the entire content of which is hereby incorporated by reference.

BACKGROUND

This disclosure pertains to methods and systems for real-time visualization of skin manipulations, such as dermal filler injections, cream or lotion application, skin resurfacing, or similar manipulations, using non-invasive optical coherence tomography (OCT) and for assessing dermal elasticity before and after the skin manipulations using optical coherence elastography (OCE).

Manipulating the skin is the basis for a vast and growing industry. As an example, dermal fillers are a popular anti-aging treatment with an estimated sales of billions of dollars and over 2 million procedures performed in the USA in 2013. As an aging population continues to increase, these figures are only expected to grow in the coming years. Topical skin rejuvenation treatments such as facial creams and chemical peels are available, but their ability to provide rapid, dramatic, and durable results is surpassed by dermal fillers. Treatments such as $CO_2$ laser resurfacing are invasive and are unable to remove larger wrinkles and furrows, which can be easily treated with dermal fillers. Botulinum toxin is the only facial treatment more popular than dermal fillers, but its effects are only noticeable in areas where there is frequent muscular motion and is not useful for reshaping. Only surgical procedures that are typically invasive can provide possibly better results to dermal fillers.

Dermal filler treatments typically last from months to years, depending on the composition, with most FDA approved dermal fillers lasting in the skin for 6 to 12 months. Furthermore, adverse reactions to dermal fillers are usually rare and most are mild and superficial with no permanent effects. However, embolic stroke and blindness as well as local ischemic reactions have been reported when fillers are inadvertently injected into the intravascular space. Currently, there are multiple FDA approved dermal fillers with varying compositions, including collagen, synthetic polymers, and hyaluronic acid.

Different dermal fillers are designed for optimal use in specific layers of the skin corresponding to different degrees of treatment. Dermal fillers, as mentioned, can carry significant risk to the patients including embolic phenomena if inadvertently injected into vascular system like the facial artery or vein, which could cause an ischemic event and blindness or stroke. Thus, real-time visual 2D and/or 3D spatial feedback would be greatly beneficial to the physician while performing the injection. Currently, there is no method which can provide real-time visual feedback to the physician with micrometer spatial resolution and predictive outcomes based on location and viscoelastic data that can be based on predictive algorithms utilizing the fillers' physical properties (e.g. stiffness, viscosity, swelling pressures, etc.). Ultrasound imaging has been used previously to provide evaluations of dermal filling procedures and to locate improper dermal injections so treatments such as nitroglycerin and hyaluronidase could be better directed to localize and aid in modifying these complications. However, acoustic imaging techniques cannot provide micrometer-scale spatial resolution and often have relatively poor contrast. Furthermore, the use of ultrasound imaging as a real-time visual feedback tool during dermal filler injections is limited by the physical presence of the transducer and transmission medium. Other imaging modalities such as x-ray computed tomography, magnetic resonance imaging (MRI), and positron emission tomography (PET) have also been used for assessing the quality of the dermal filler. However, these methods can be excessive for dermal filler injection evaluation and impractical for real-time imaging. Ultrasound and OCT have been used in the field of dermatology to apply energy to the subcutaneous skin to effect new collagen formation, but not for real-time imaging or evaluations of dermal filler injections.

SUMMARY

The present disclosure relates generally to methods and systems for real-time 3D visual feedback and elasticity assessment of the skin to optimize the placement, volume, and choice of viscosity of skin manipulations such as dermal filler injections, cream or lotion applications, and skin resurfacing using optical coherence tomography (OCT) and optical coherence elastography (OCE) and to continuously see a virtual and real time end result after injection.

In one exemplary application, dermal fillers are currently injected into the patient qualitatively only by visual inspection from the physician or aesthetician, and the elasticity of the skin is not quantified before and after the injection. By using the method and the viewing system, visualization of the injection process as well as imaging of the final result is possible in real-time with micrometer precision. By utilizing an air-pulse and phase-resolved optical coherence elastography system in conjunction with an analytical model-based displacement reconstruction model, quantitative evaluation of the viscoelasticity of the skin before and after the injection is possible. This dramatically enhances the precision of the injections, i.e. the exact volume amounts that are needed to provide the proper contours and depths needed to effect the necessary changes, and provides 2- or 3D real time quantitative feedback to the individual doing the facial sculpting injection. This process can be viewed before (after obtaining the mechanics of the skin) and after the actual injections so both physician and patient can see a simulated virtual end result based on the patient's elastography of the skin and simulated 2-3D projection, so both virtual and real-time injection would eventually match each other for the perfect pre-injection virtual expectation. The present methods offer greater precision and safety when using dermal fillers or when crosslinking these fillers in areas like the vermillion of the mouth or lower eye lid troughs. These areas of the face currently are inadequately addressed, and when injection localization has micrometer-scale precision, the potential aesthetic results will be exponentially improved.

Optical coherence tomography (OCT) is a well-established optical imaging technique based on low coherence interferometry. OCT utilizes broadband light to provide high-contrast depth-resolved imaging with micrometer-scale spatial resolution and can penetrate up to a few millimeters in tissues such as skin. Typically, in the present system, the penetration is between about 1 to 2 mm. However, variables such as incident power, attenuation coefficient, scattering coefficient, polarization, and others can change the range of penetration from a few hundred microns up to several millimeters. Light from a broadband laser source is split into reference and sample arms directed at a mirror and the sample of interest, respectively. The backscattered light from the sample is collected and combined with the reflected light from the reference arm and an interference pattern is formed. The interference pattern is then captured and converted into a single depth-resolved A-line by a Fourier transform. Volumetric imaging is usually performed by scanning the beam across the sample with galvanometer-controlled mirrors. Recent developments in optical hardware, such as Fourier Domain Mode Locked lasers, and computing, such as graphics processing unit accelerated software, have made real-time video rate 3D acquisition and visualization possible.

OCT can also be used to obtain the local mechanical properties of a sample through optical coherence elastography (OCE). Similar to other elastographic methods, such as ultrasound elastography and magnetic resonance elastography, OCT can be used to image displacements in a sample induced by an external loading force. By analyzing the phase of the complex OCT signal, OCE can detect displacements on the order of nanometers, which enables the use of a minimal excitation force. This helps preserve the function and structure of tissues and has enabled the use of OCE to study the biomechanical properties of various tissues such as bioengineered tissue, skin, atherosclerotic tissues, cartilage, crystalline lens, and cornea. Although the rheological properties of dermal fillers have been evaluated, there has been no direct study of the effects of dermal filler injections on the biomechanical properties of skin. This is also important for different locations of the face where the dynamic elastic properties vary based on location, i.e. skin of the eyelid vs. the forehead vs. the upper lip. Moreover, the dynamic elastic properties will vary with age and the historical milestones as a result of previous trauma, skin treatments, and surgery. 2- or 3D imaging incorporating the dynamic elastography will help in improving the precision and location and predictive final outcomes of each series of dermal fillers viscosity options and final virtual projected results and ultimate final results.

The present disclosure relates to methods and systems for providing depth-resolved real-time qualitative and quantitative visual feedback to a physician during skin manipulations such as cosmetic dermal filler injections with micrometer spatial resolution using a noninvasive imaging system in 2D and 3D. The present disclosure also includes a method for assessing the elasticity of the tissue before and after the manipulation to evaluate the qualitative and quantitative efficacy of, for example, the injection and projection of the final pre and post injection results. The elasticity assessment method utilizes a focused air-pulse to induce a micrometer scale displacement in the skin and the optical coherence tomography system to image this displacement. By utilizing a model-based reconstruction method, i.e. 3D reconstruction, before and after injection in local or all areas of the face, a pre injection with known volumes and dermal filler injection qualities can be pre-determined before injection and visualized during and post injection in a real time fashion. The viscoelasticity of the tissue at a specific measurement position on the areas of interest, i.e. lip, glabellar region, eye lids, "crows feet," etc. is obtained from the temporal deformation profile. By comparing the skin viscoelasticity before, during, and after the injection, the physician can determine whether further treatment is necessary to match predetermined virtual imaged endpoints to effect a final 3D image of a predetermined result. The facial skin can also be evaluated over an extended period of time to determine the necessity for follow-up refinement and treatment. A combined focused air-pulse delivery device and optical coherence tomography/elastography system and 2-3D imaging are also disclosed.

The present disclosure relates to methods and systems which could be combined with facial photography with oblique illumination, direct or indirect.

The present disclosure relates to methods and systems which can combine micro/macro/topography (i.e. lines and valleys sculpting, colors) and elastography to know where to create points of injection in the most dynamically movable topography of the skin (explosion points vs. fixation points) in the brow area, periorbital regions, the upper eyelid region and the area between the brow and the skin of the upper lid, the lower lid region (a specialized area), along the zygoma, and midface.

The present system and method can be used with variety of different facial altering modalities such as radio frequency for internal contraction, intense pulsed light more for colors and wrinkles, fillers with cross linking and nano needle technology for variable macro and micro filling, BOTOX® (onabotulinumtoxinA), or more long term agents or muscle agonist for area of dynamic creasing, i.e. "crows feet" or smokers creases.

Using OCT and dynamic 2-3D imaging will provide additional safety to the blind approaches that are currently used for dermal filler injections. Additionally, parotid duct cyst and obstruction would be minimized with this type of imaging and improve safety of these types of procedures.

DETAILED DESCRIPTION OF PREFERRED EMBODIMENTS

The present disclosure relates to methods and systems for providing real-time visual feedback of skin manipulations such as dermal filler injections with micrometer spatial resolution by optical coherence tomography (OCT) and elastographic evaluation using optical coherence elastography (OCE). Due to the noninvasive nature of OCT and recent advances in optical hardware enabling video rate volumetric imaging, OCT is useful for evaluation of dermatological cosmetic procedures. Combining OCT with an external loading mechanism also enables elastographic evaluation of the skin by OCE. By utilizing the superior displacement sensitivity of OCE to detect the skin deformation by a focused air-pulse, a noninvasive assessment method of the biomechanical properties of the skin before and after dermal filler injection has been developed. Furthermore, utilizing a viscoelastic reconstruction model, quantification of the biomechanical properties of the skin and localization of the dermal filler injection sites has been accomplished.

Currently, physicians have no real-time visual feedback with micrometer resolution while injecting dermal fillers or techniques of noninvasively quantifying the elasticity changes after the injection. Embodiments of the present method and system provide real-time visual feedback with micrometer spatial resolution by optical coherence tomography (OCT) and elastographic evaluation using optical coherence elastography (OCE). An OCT system can be used to visualize dermal filling injections in real-time, preferably at 30 frames per second or more (video-rate). An OCT system can be combined with a focused air-pulse delivery device, or any other excitation method such as acoustic radiation force, direct indentation with force transducers, or light, electrical and magnetic forces, to assess the elasticity of the skin by OCE. By utilizing the phase of the OCT signal, sub-micrometer scale displacements can be detected, which ensures preservation of the structure and function of the tissue and possible minimization of patient discomfort.

The rate of relaxation and spectral analysis of the dynamically induced displacement can be analyzed to provide an assessment of elasticity changes in the skin. Furthermore, in certain embodiments, a mechanical model was employed to quantify the viscoelasticity of the skin based on the air-pulse induced displacement profile. The elasticity of the skin was assessed at different locations and a 2D elasticity map was generated. The model-based viscoelasticity reconstruction showed an increased elasticity and viscosity at the sites of the injection as compared to surrounding tissue. The present method and system are useful in clinical applications to provide visual and viscoelastic feedback to increase efficacy during injection of the dermal filler.

Generally, embodiments of the present method include a method for identifying locations of and quantifying effects of a skin manipulation such as a dermal filler injection, or the cross-linking of a filler injection, on an area of skin having been treated, presently being treated, or expected to be treated, comprising the steps of producing an external force to stimulate localized deformations on a plurality of locations on the area of skin, using an optical coherence elastography (OCE) system to measure temporal displacement profiles resulting from the localized deformations on the plurality of locations on the area of skin, quantifying biomechanical properties of the plurality of locations on the area of skin based on an analysis of the temporal displacement profiles; and mapping one or more biomechanical properties of the plurality of locations on the area of skin to identify the locations of and quantify the effects of the dermal filler injection or filler cross-linking on the area of skin.

In preferred embodiments, the step of producing an external force to stimulate localized deformations is performed by any suitable system for delivering an external force to a particular location and is preferably by using focused air pulses at each of the desired locations on the area of skin. This step can be performed by any appropriate method, such as ultrasonic excitation, acoustic radiation force stimulation, or mechanical indentation. The plurality of locations on the area of skin include locations with a dermal filler injection and without a dermal filler injection. The biomechanical properties that are quantified can be one or more of axial displacement, relaxation rate, relaxation process, frequency of the relaxation process, spectral properties, Young's modulus, elasticity, and viscosity. In additional embodiments, the method may also include the step of visualizing the dermal filler injection as the injection is occurring, or visualizing changes in the skin and the filler during injection and/or cross-linking, using an optical coherence tomography (OCT) system. In certain embodiments, the steps are first performed on an area of skin prior to treatment with a dermal filler injection and then repeated on the same area of skin after treatment with the dermal filler injection. In other embodiments, the steps are first performed on an area of skin after a dermal filler injection and then repeated on the same area of skin after cross-linking of the filler.

Additional embodiments relate to a system for identifying locations of and quantifying effects of a skin manipulation such as a dermal filler injection, or the cross-linking of a dermal filler, on an area of skin in which the dermal filler has been injected, comprising an external force delivery subsystem for producing an external force to stimulate localized deformations on a plurality of locations on the area of skin, an optical coherence elastography (OCE) system for measuring temporal displacement profiles resulting from the localized deformations on the plurality of locations on the area of skin, and a data processor programmed to quantify biomechanical properties of the plurality of locations on the area of skin based on an analysis of the temporal displacement profiles and to map one or more biomechanical properties of the plurality of locations on the area of skin to identify the locations of and quantify the effects of the dermal filler injection on the area of skin. The system may further comprise an optical coherence tomography (OCT) system for visualizing the skin in 2D and/or 3D before and after dermal filler injections, or before and after dermal filler cross-linking, or while the injection or the cross-linking is taking place.

Additional embodiments relate to a system capable of direct visualizing and biomechanical assessment of wrinkles that have been treated and have temporal depth and direct imaging of the virtual pre-injection and post-injection results.

EXAMPLE 1

Visualization

Figure 1:
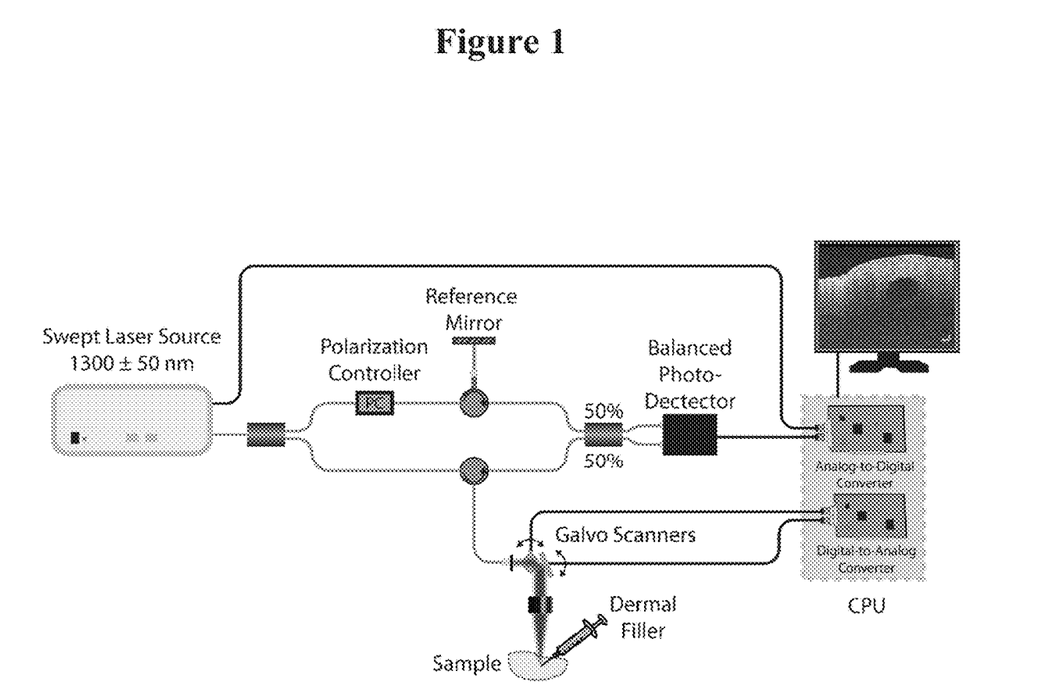
FIG. 1 shows a schematic of an example swept source optical coherence tomography (SS-OCT) system that can be used during dermal filler injection visualization.

A commercial swept source OCT system (SS-OCT) (Model OCS1310V1, Thorlabs Inc., NJ, USA) with a scan rate of 200 kHz, central wavelength of 1300 nm, bandwidth of ~100 nm, and axial resolution of ~16 μm in air was utilized to image a dermal filler injection. A schematic of the SS-OCT system is shown in FIG. 1.

Dermal filler (Juvederm® Ultra XC, Allergan Inc., CA, USA) was injected ~1 mm below the surface at three locations into pig skin obtained from a local grocery store. The swept source OCT system continuously acquired 2D B-scan images of 1000 A-lines each during the injection, resulting in an acquisition speed of 200 frames per second. After injection, three dimensional OCT structural images were acquired by the SS-OCT system to evaluate the injection.

Figure 2:
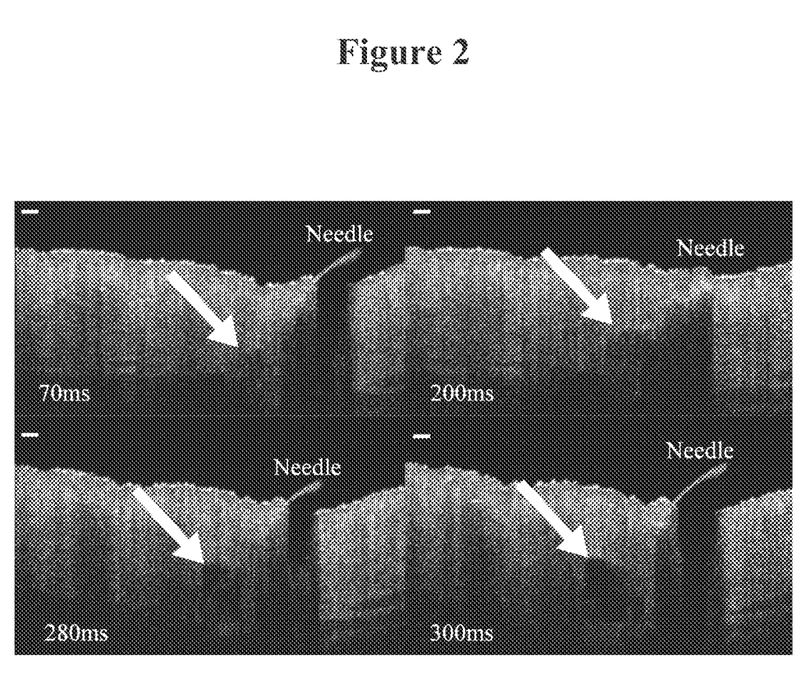
FIG. 2 shows typical optical coherence tomography (OCT) images acquired during a dermal filler injection, with scale bars of 250 µm.
Figure 3:
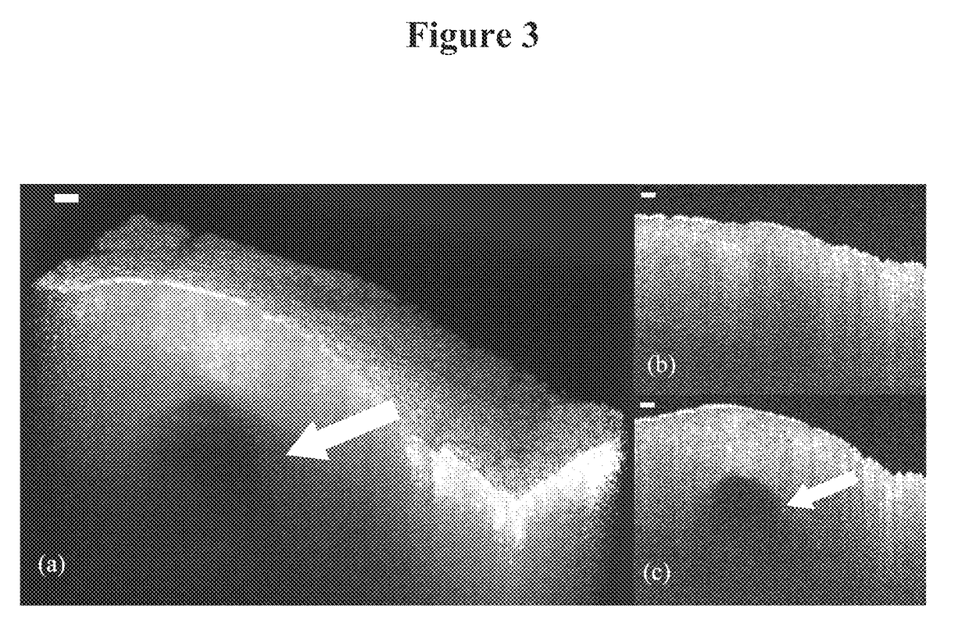
FIG. 3 shows (a) 3D visualization of pig skin after a dermal filler injection, (b) 2D slice of the skin where no dermal filler was injected, and (c) 2D slice of the skin showing the presence of the dermal filler, with arrows indicating the location of the dermal filler and scale bars of 250 µm.

The dermal filler injection process was successfully visualized by the SS-OCT system. Selected individual frames during the injection are shown in FIG. 2. The injection needle and dermal filler can clearly be seen and the precise depth of the injection can be easily controlled by the physician with micrometer precision with OCT as a real-time visual feedback tool. After injection, a volume was acquired to investigate the injection, which is displayed in FIG. 3. FIG. 3(a) is a 3D rendering of the skin showing the injection site of the dermal filler. FIGS. 3(b) and (c) are slices corresponding to the furthest and nearest slices of FIG. 3(a), respectively. Assuming the injected volume is a sphere, the OCT image shows that ~0.5 mm$^3$ was injected ~1 mm below the pig skin surface.

These results demonstrate the use of OCT as a visual feedback tool with micrometer resolution during dermal filler injections. Utilizing an OCT system, the injection process was visualized for the first time with micrometer resolution in real-time at 200 frames per second, albeit in only 2D. Although OCT typically uses wavelengths in the near infrared because these were adopted by the telecommunications industry, which increases the availability of optical hardware and reduces cost, increased imaging depth can be achieved with longer wavelengths as well as optical clearing methods, which require the use of a clearing medium.

EXAMPLE 2

Elasticity Assessment

Figure 4:
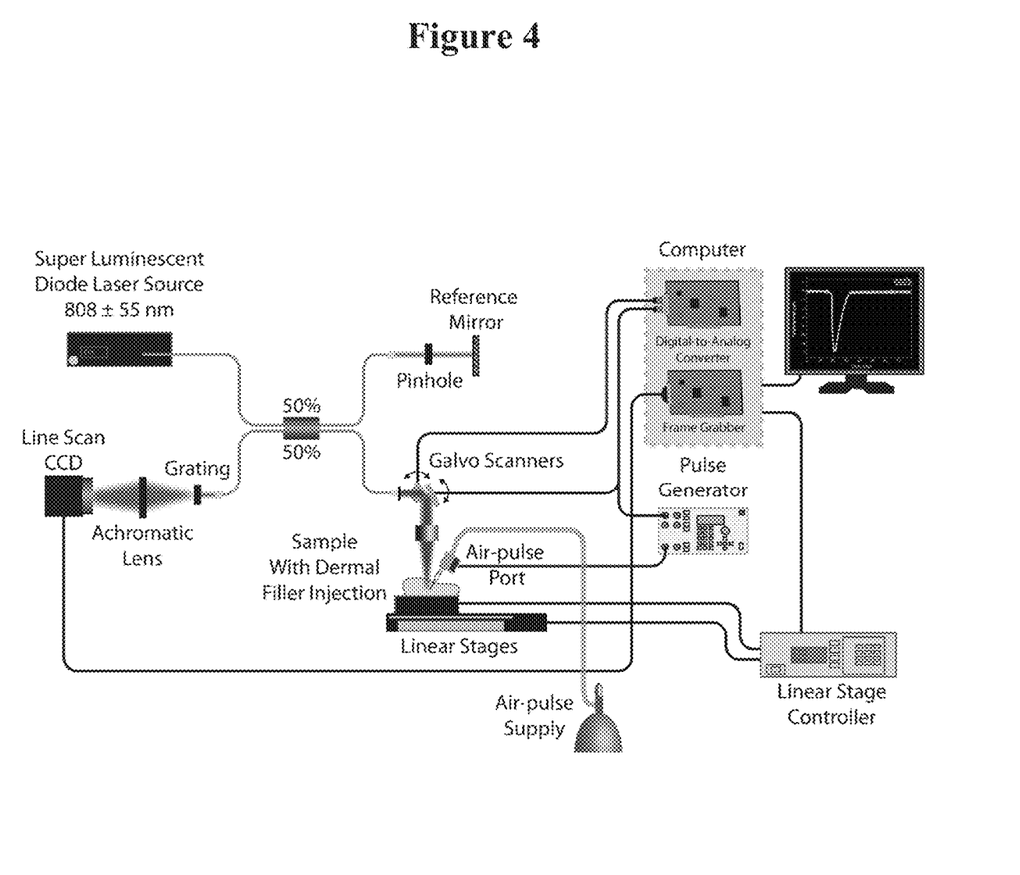
FIG. 4 shows a schematic of an example optical coherence elastography (OCE) setup for skin elastographic evaluation after dermal filler injection.

A custom built phase-sensitive OCE system was utilized to assess the elasticity of the pig skin injected with dermal filler as discussed in Example 1. A spectral domain OCT (SD-OCT) system with an A-line rate of 62.5 kHz, a central wavelength of ~808 nm, a bandwidth of ~110 nm, and an axial resolution of ~7 μm in air was combined with a custom built focused air-pulse delivery device. A short duration (≤1 ms) focused air-pulse with a Gaussian temporal profile was expelled out of a solenoid controlled air gate. The air gate had a flat edge and an inner diameter of ~150 μm. The air-pulse system was synchronized with the SD-OCT system by a transistor-transistor logic (TTL) signal. The OCT imaging beam was co-focused with the air-pulse during all OCE measurements. The tip of the air port was kept ~250 μm away from the surface of the skin to prevent the influence of near-field effects. The sample was mounted on a pair of motorized linear stages (Model UTS100CC, Newport Inc., CA, USA) for accurate translation while generating the 2D elasticity maps. A schematic of the OCE setup is shown in FIG. 4.

The pig skin was then evaluated by OCE with the SD-OCT system. An area of 45 mm by 15 mm of 10 points by 4 points, respectively, was measured on the pig skin. A larger region was measured but areas of the pig skin with insufficient thickness were excluded due to the requirement of the viscoelastic model. Focused air-pulses were delivered to the surface of the pig skin at ~20 Pa at each of the measurement positions. M-mode images (n=21) were acquired at each measurement position and each air-pulse was synchronized with each M-mode frame trigger. The temporal displacement profiles were analyzed for their relaxation rate, spectral properties, and for viscoelasticity reconstruction. The axial displacement, d(t), was obtained by:

$$d(t) = \phi(t) \times \frac{\lambda_0}{4\pi},$$

where ϕ(t) is the measured phase profile and $\lambda_0$ is the central wavelength of the SD-OCT system.

Figure 5:
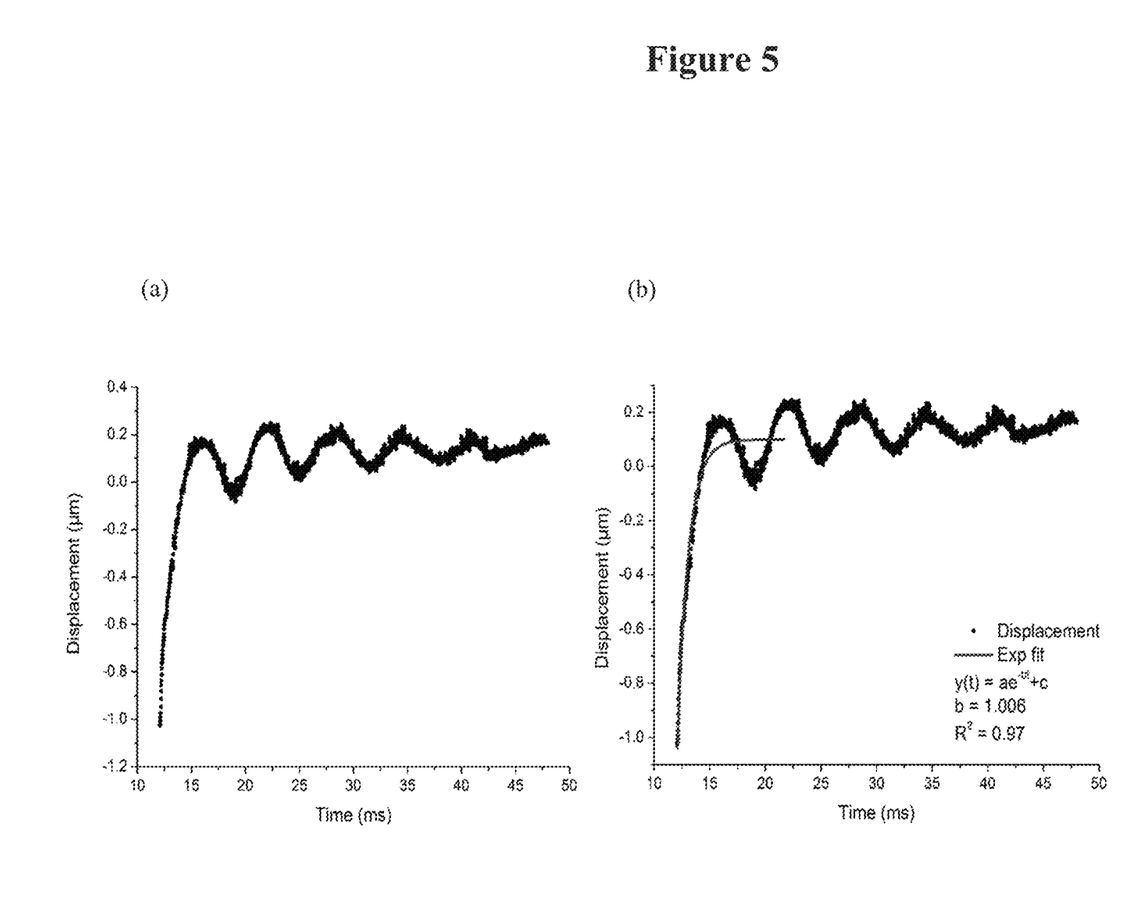
FIG. 5 shows (a) a typical temporal displacement profile as measured by optical coherence elastography (OCE), and (b) a relaxation process and fit of the temporal displacement profile shown in (a).
Figure 6A:
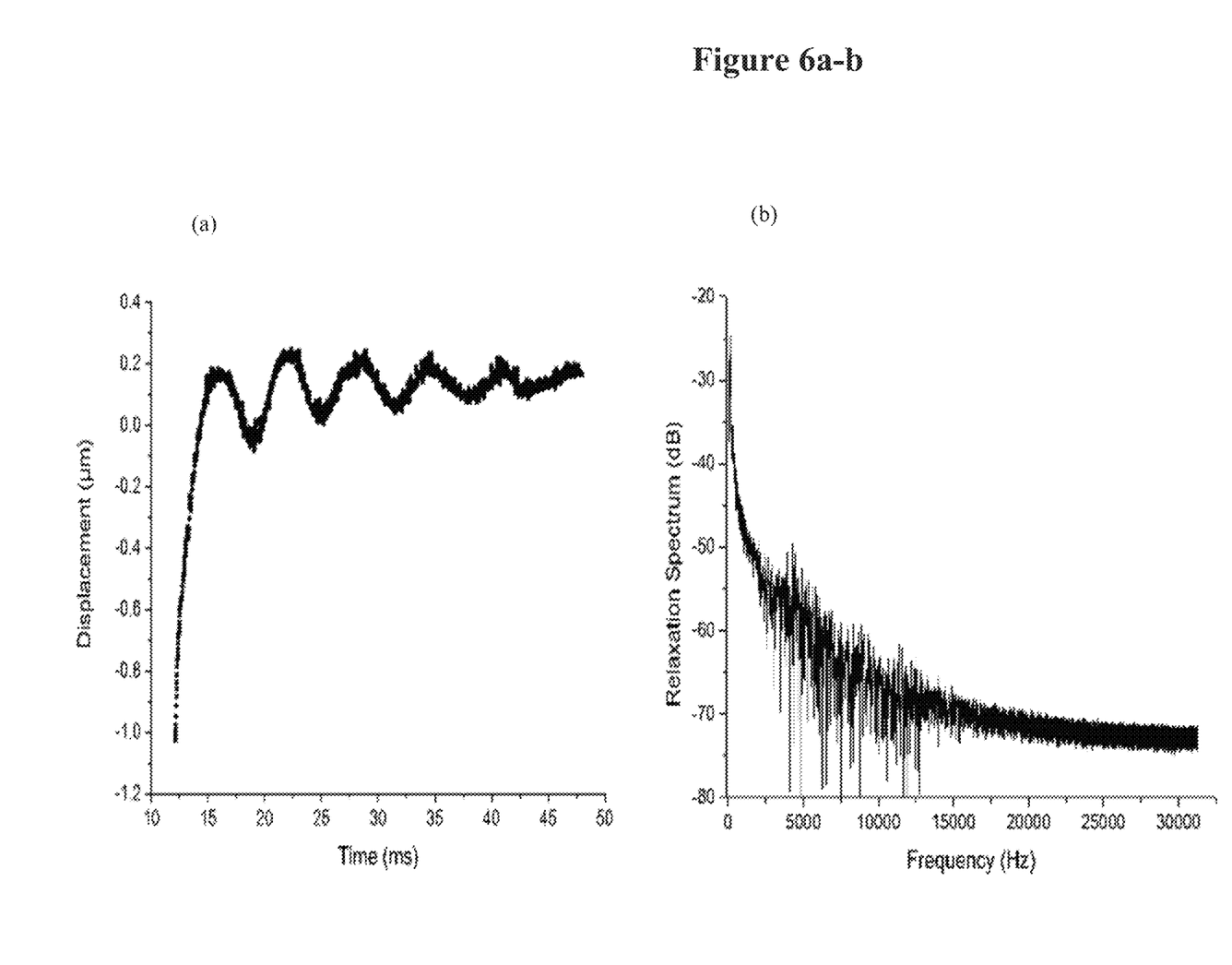
FIG. 6 shows (a) a relaxation process as measured by optical coherence elastography (OCE), (b) a relaxation process spectrum, and (c) a relaxation process spectrum (0-1 kHz) showing the dominant frequency of the relaxation process.
Figure 6C:
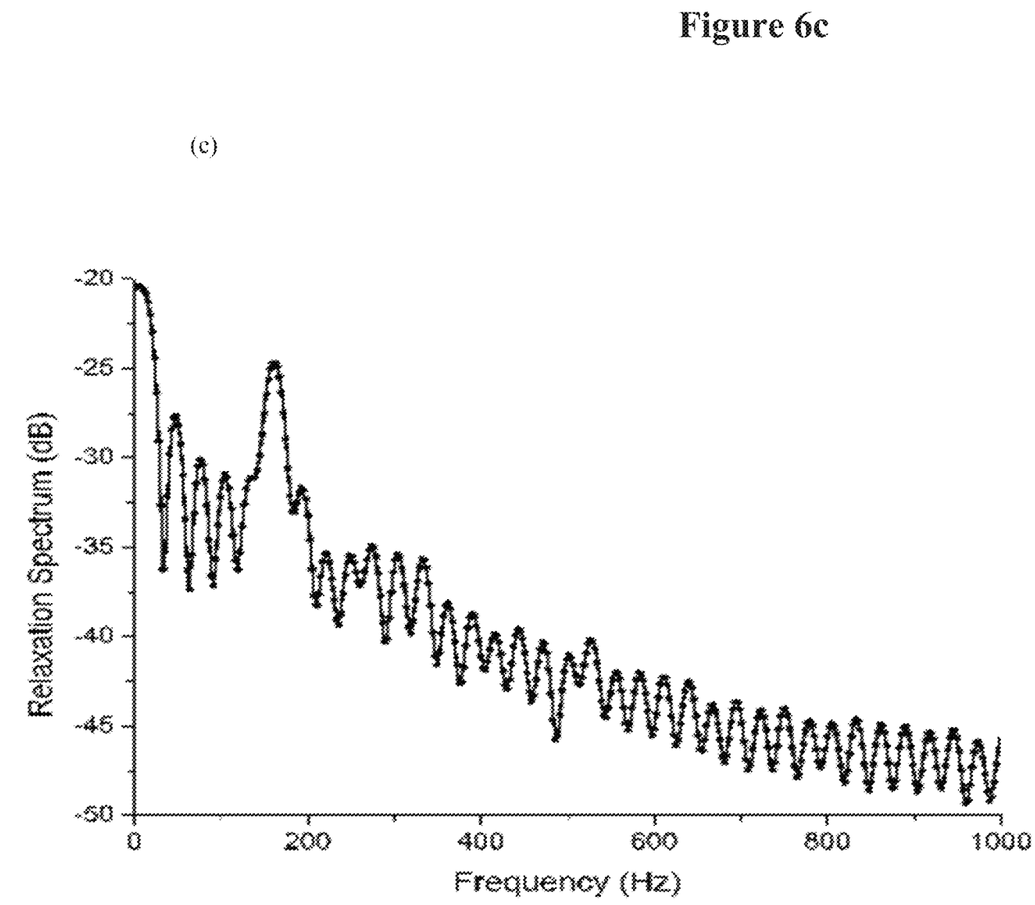

The relaxation process, y(t), was fitted by:

$$y(t) = ae^{-bt} + c,$$

where b is the relaxation rate to be determined, as shown in FIG. 5. FIG. 5(a) shows the typical temporal displacement profile and FIG. 5(b) shows the relaxation process and fit of temporal displacement profile in 5(a). The spectral properties of the relaxation process were analyzed by performing a fast Fourier transform (FFT) on the relaxation process temporal displacement profile as depicted in FIG. 6. The displacement profile was zero padded by a factor of ten to increase spectral resolution. The dominant frequency was then identified and plotted for each measurement position. FIG. 6(a) shows the relaxation process as measured by OCE, FIG. 6(b) shows the relaxation process spectrum, and FIG. 6(c) shows the relaxation process spectrum (0-1 kHz) showing the dominant frequency of the relaxation process.

A modified viscoelasticity model was utilized to quantify elasticity and viscosity based on the normalized temporal displacement profiles. The normalization was conducted to remove the influence of variations in acoustic impedance and the air-pulse pressure. Therefore, only the spectral characteristics of the displacement profiles were utilized, ignoring the influence of the deformation amplitude on the elasticity reconstruction. The tissue was modeled as a nearly incompressible viscoelastic (Kelvin-Voigt) homogeneous and isotropic structure with infinite depth. An analytical solution of the vertical displacement profile after external loading at angular frequency, ω, in the frequency domain can be expressed in cylindrical coordinates (r,θ,z) using:

$$U_z(r, z, \omega) = \int_0^\infty [\alpha(A_1 e^{-\alpha z} + A_2 e^{\alpha z}) + k(B_1 e^{-\beta z} + B_2 e^{\beta z})] J_0(kr) k \, dk,$$

$$\text{where: } \alpha^2 = k^2 - \frac{\omega^2}{c_1^2}, \beta^2 = k^2 - \frac{\omega^2}{c_2^2}, c_1 = \sqrt{\frac{\lambda + 2\mu}{\rho}}, c_2 = \sqrt{\frac{\mu}{\rho}}.$$

Here, k was the wave number, $J_0$ and $J_1$ were the 0 and 1 order Bessel functions, and λ and μ were the Lame constants with λ=Ev/((1+v)(1-2v)) and μ=E/(2(1+v)) with v being the Poisson ratio. The shear viscosity and Young's modulus are included in the dynamic modulus, E. The skin density was ρ and $c_1$ and $c_2$ were the compressional and shear wave velocities, respectively. Boundary conditions defined the unknown constants $A_1$, $A_2$, $B_1$, and $B_2$: an angled load to the top surface at the co-focused position of the excitation and OCE measurement, no shear force on the top surface, and an infinite depth for the bottom surface. The displacement profile was reconstructed with different elasticity and viscosity values using a gradient iterative process where the error between the reconstructed displacement profile and OCE measured displacement profile was minimized.

Figure 7A:
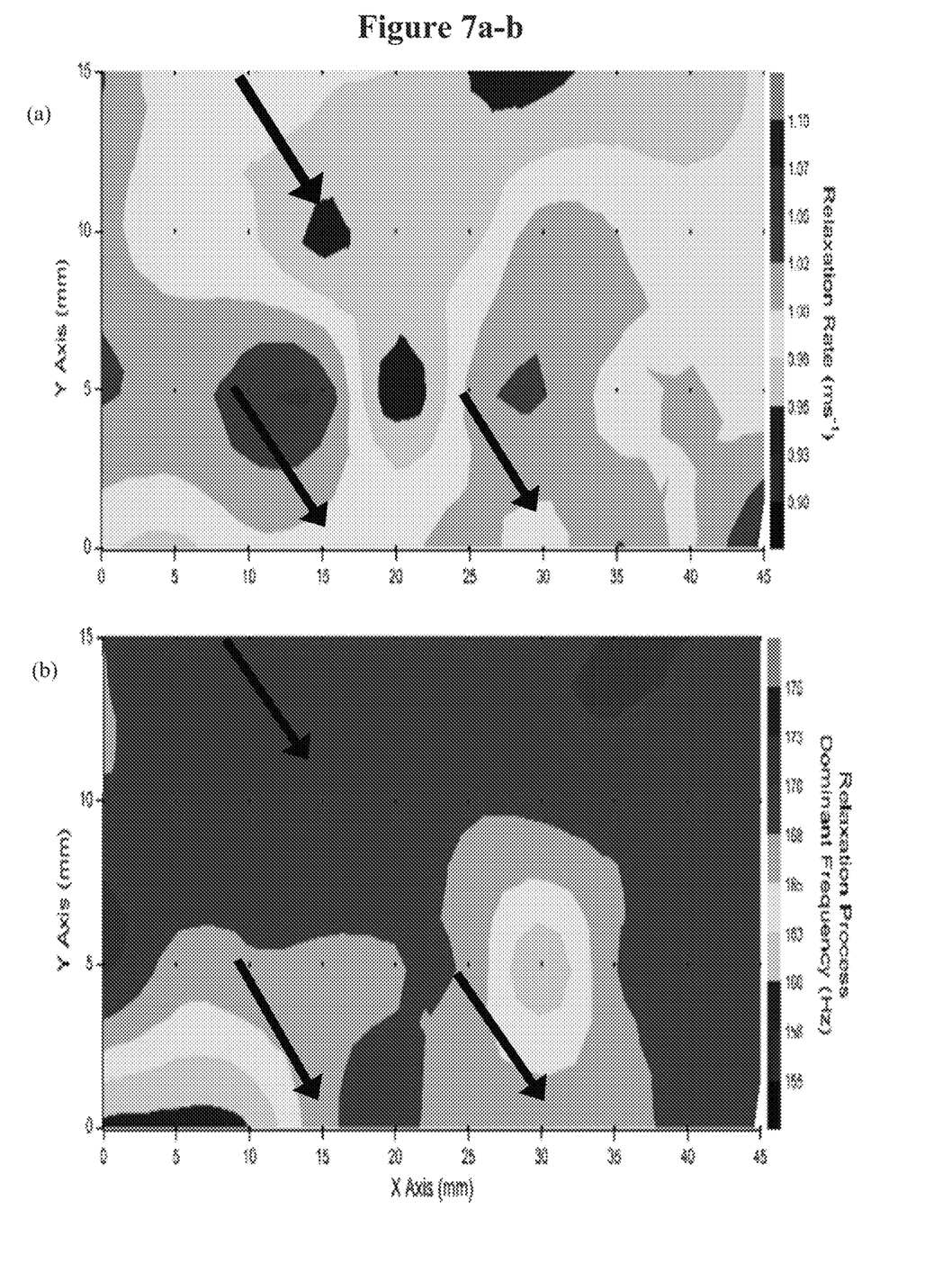
FIG. 7 shows 2D maps of (a) a relaxation rate of the displacement induced by a focused air-pulse, (b) the dominant frequency of the relaxation process, (c) Young's modulus obtained from the viscoelasticity reconstruction model, and (d) viscosity obtained from the viscoelasticity reconstruction model, with arrows indicating positions of the dermal filler injections and black dots indicating OCE measurement positions.
Figure 7C:
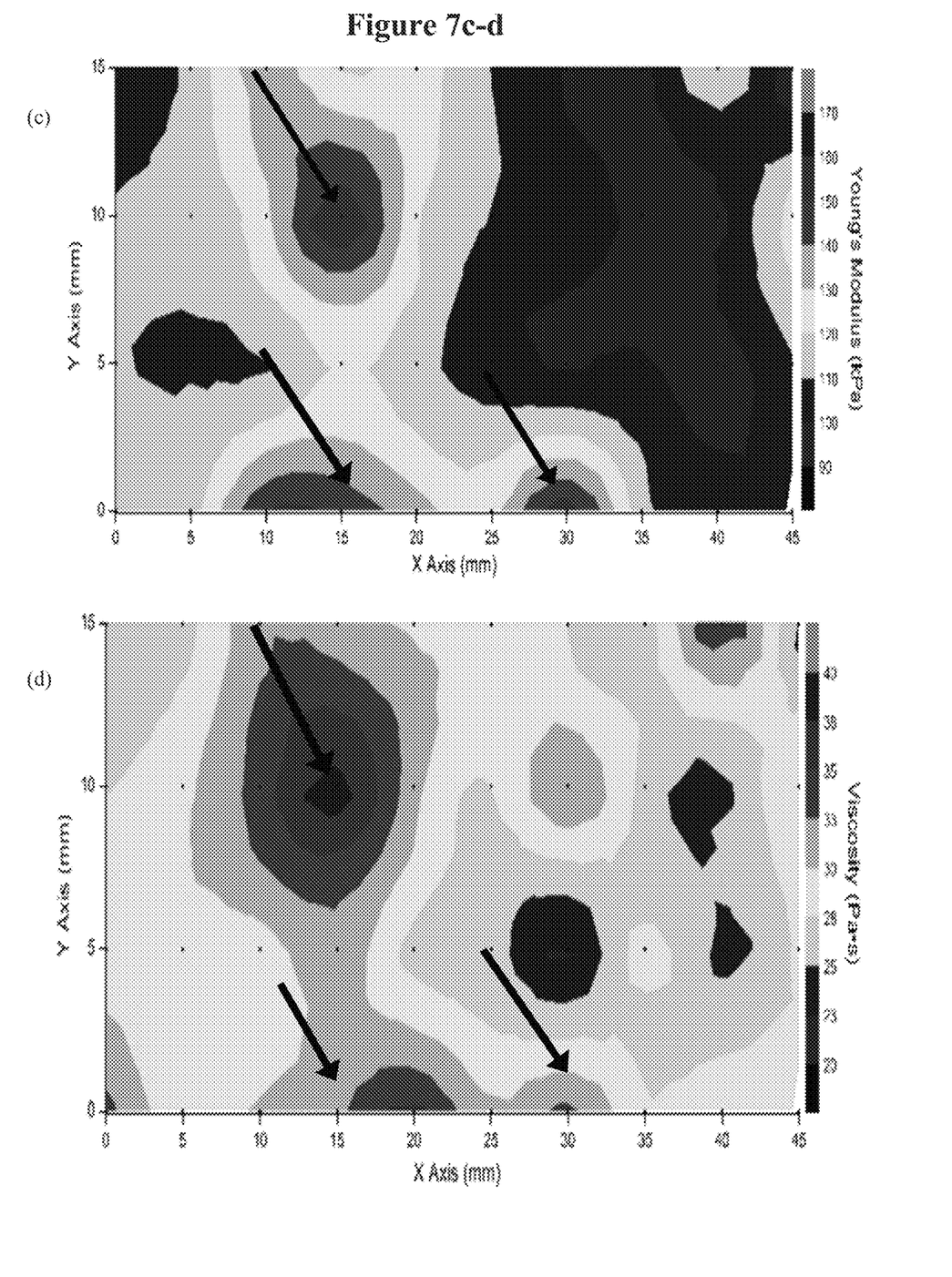
Figure 8:
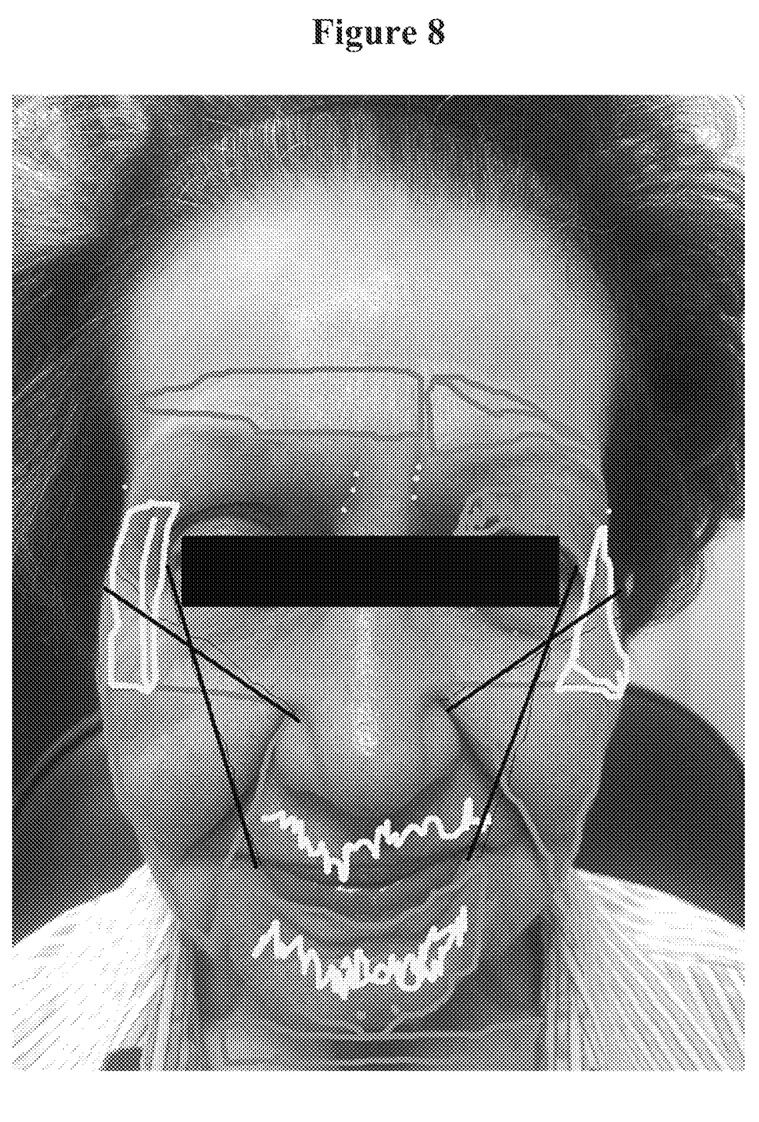
FIG. 8 shows an example of facial/neck features which will benefit from the present method and system with OCT/OCE reconstructions, before and after injection in local or all areas of the face, of a pre injection with known volumes and dermal filler injection qualities.

The elasticity of the skin was assessed by analyzing the relaxation process of the skin after mechanical loading by a focused air-pulse. The 2D maps of the biomechanical properties of the pig skin are shown in FIG. 7, with the black arrows indicating the positions of the dermal filler injections and the black dots depicting the OCE measurement positions. FIG. 7(a) shows a 2D map of the relaxation rates that were calculated by fitting the relaxation process to the y(t) equation as shown in FIG. 5(b). From the relaxation rate map, the locations of the injection sites are not evident. The average relaxation rate for all data points (n=945) was $0.99 \pm 0.048$ ms$^{-1}$, indicating a low variance within the samples and subsequent lack of dermal filler localization. From the relaxation process, high frequency oscillations were observed as seen in FIG. 5 and FIG. 6(a). From this observation, the spectrum of the relaxation process was obtained by performing a FFT on the temporal displacement profile of the relaxation process and mapping the dominant frequency for each OCE measurement position, which is shown in FIG. 7(b). For all OCE measurement positions, the mean relaxation process dominant frequency was $168 \pm 6.4$ Hz, indicating a low variance between all measurement positions once again. Using the temporal displacement profile viscoelasticity reconstruction model, the elasticity and viscosity were also mapped, as depicted in FIGS. 7(c) and (d), respectively. The average elasticity was $117 \pm 24$ kPa and the average viscosity was $29.6 \pm 5.2$ Pa·s.

The elastic properties of the skin were quantified by OCE. Utilizing the relaxation rate, the dermal filler injection sites could not be localized. This is likely due to the effects of the depth of injection. As the air-pulse induced displacement is on the order of micrometers and the thickness of the skin is on the order of centimeters, the elasticity assessment method by relaxation rate may only provide the elasticity of the surface of the skin. Other methods of elasticity assessment which can account for the depth-wise elasticity effects must be utilized. After selecting the dominant frequency of the relaxation process, the locations of the dermal filler injections still could not be localized. However, utilizing the reconstruction model, the dermal filler injection sites were localized from the increased elasticity and viscosity as compared to surrounding tissues. Other sites of increased elasticity may be artifacts due to variations in the pig skin itself and boundary conditions. Furthermore, the reconstruction model assumes the sample has an infinite depth, which is a valid assumption as the micrometer scale displacement is orders of magnitude smaller than the thickness of the pig skin. Regions of the pig skin which were very thin at the periphery of the sample were excluded due to the infinite depth requirement of the model and subsequent inaccurate viscoelastic quantification. Nevertheless, the elasticity values obtained were similar to those obtained of human skin by OCE.

Dermal fillers are not intended to directly alter the elasticity of the skin, only reduce the presence of lines and wrinkles by adding volume in or beneath the skin. Nevertheless, the additional volume beneath the skin exerted a stress, and therefore strain on the skin, altering the elasticity of the skin. Even though dermal fillers are softer than skin, the additional stress increased the elasticity of the skin. The increase in elasticity at a greater stress was due to the nonlinearity of the stress-strain curve of the pig skin. Therefore, with additional stress, the elasticity of the skin increased.

REFERENCES

The following references, to the extent that they provide exemplary procedural or other details supplementary to those set forth herein, are specifically incorporated herein by reference.

A. Blitzer, M. F. Brin, M. S. Keen et al., "Botulinum toxin for the treatment of hyperfunctional lines of the face," Archives of Otolaryngology-Head & Neck Surgery, 119 (9), 1018-1022 (1993).

D. Bray, C. Hopkins, and D. N. Roberts, "A review of dermal fillers in facial plastic surgery," Current opinion in otolaryngology & head and neck surgery, 18(4), 295-302 (2010).

S. S. Johl, and R. A. Burgett, "Dermal filler agents: a practical review," Current opinion in ophthalmology, 17(5), 471-479 (2006).

N. J. Lowe, C. A. Maxwell, and R. Patnaik, "Adverse reactions to dermal fillers: review," Dermatologic surgery, 31(s4), 1626-1633 (2005).

D. Ginat, and C. Schatz, "Imaging features of midface injectable fillers and associated complications," American Journal of Neuroradiology, 34(8), 1488-1495 (2013).

M. Romagnoli, and M. Belmontesi, "Hyaluronic acid-based fillers: theory and practice," Clinics in Dermatology, 26(2), 123-159 (2008).

F. R. Grippaudo, and M. Maffei, "High-frequency sonography of temporary and permanent dermal fillers," Skin Research and Technology, 16(3), 265-269 (2010).

F. A. Roldan, "Ultrasound Skin Imaging," Actas Dermo-Sifiliograficas (English Edition), (2014).

L. W. Schelke, H. J. Van Den Elzen, P. P. M. Erkamp et al., "Use of Ultrasound to Provide Overall Information on Facial Fillers and Surrounding Tissue," Dermatologic Surgery, 36, 1843-1851 (2010).

X. Wortsman, "Common applications of dermatologic sonography," Journal of Ultrasound in Medicine, 31(1), 97-111 (2012).

X. Wortsman, J. Wortsman, C. Orlandi et al., "Ultrasound detection and identification of cosmetic fillers in the skin," Journal of the European Academy of Dermatology and Venereology, 26(3), 292-301 (2012).

S. Young, P. Bolton, and J. Downie, "Use of high-frequency ultrasound in the assessment of injectable dermal fillers," Skin Research and Technology, 14(3), 320-323 (2008).

D. Huang, E. A. Swanson, C. P. Lin et al., "Optical coherence tomography," Science, 254(5035), 1178-1181 (1991).

R. Huber, M. Wojtkowski, and J. G. Fujimoto, "Fourier Domain Mode Locking (FDML): A new laser operating regime and applications for optical coherence tomography," Optics Express, 14(8), 3225-3237 (2006).

K. Zhang, and J. U. Kang, "Real-time 4D signal processing and visualization using graphics processing unit on a regular nonlinear-k Fourier-domain OCT system," Optics Express, 18(11), 11772-11784 (2010).

M. R. Hee, J. A. Izatt, E. A. Swanson et al., "Optical coherence tomography of the human retina," Archives of ophthalmology, 113(3), 325-332 (1995).

I. K. Jang, B. E. Bouma, D. H. Kang et al., "Visualization of coronary atherosclerotic plaques in patients using optical coherence tomography: comparison with intravascular ultrasound," Journal of the American College of Cardiology, 39(4), 604-609 (2002).

H. Yabushita, B. E. Bouma, S. L. Houser et al., "Characterization of human atherosclerosis by optical coherence tomography," Circulation, 106(13), 1640-1645 (2002).

M. Jenkins, F. Rothenberg, D. Roy et al., "4D embryonic cardiography using gated optical coherence tomography," Optics Express, 14(2), 736-748 (2006).

I. V. Larina, S. H. Syed, N. Sudheendran et al., "Optical coherence tomography for live phenotypic analysis of embryonic ocular structures in mouse models," Journal of biomedical optics, 17(8), 0814101-0814104 (2012).

G. J. Tearney, M. E. Brezinski, B. E. Bouma et al., "In vivo endoscopic optical biopsy with optical coherence tomography," Science, 276(5321), 2037-2039 (1997).

C. Pitris, A. Goodman, S. A. Boppart et al., "High-resolution imaging of gynecologic neoplasms using optical coherence tomography," Obstetrics & Gynecology, 93(1), 135-139 (1999).

J. Welzel, E. Lankenau, R. Birngruber et al., "Optical coherence tomography of the human skin," Journal of the American Academy of Dermatology, 37(6), 958-963 (1997).

J. A. Izatt, M. D. Kulkarni, S. Yazdanfar et al., "In vivo bidirectional color Doppler flow imaging of picoliter blood volumes using optical coherence tomography," Optics letters, 22(18), 1439-1441 (1997).

I. V. Larina, N. Sudheendran, M. Ghosn et al., "Live imaging of blood flow in mammalian embryos using Doppler swept-source optical coherence tomography," Journal of biomedical optics, 13(6), 060506-060506-3 (2008).

J. M. Schmitt, S. Xiang, and K. M. Yung, "Speckle in optical coherence tomography," Journal of biomedical optics, 4(1), 95-105 (1999).

N. Sudheendran, S. Syed, M. Dickinson et al., "Speckle variance OCT imaging of the vasculature in live mammalian embryos," Laser Physics Letters, 8(3), 247 (2011).

R. Leitgeb, M. Wojtkowski, A. Kowalczyk et al., "Spectral measurement of absorption by spectroscopic frequency-domain optical coherence tomography," Optics letters, 25(11), 820-822 (2000).

U. Morgner, W. Drexler, F. Kartner et al., "Spectroscopic optical coherence tomography," Optics letters, 25(2), 111-113 (2000).

N. Belaid, I. Cespedes, J. Thijssen et al., "Lesion detection in simulated elastographic and echographic images: a psychophysical study," Ultrasound in medicine & biology, 20(9), 877-891 (1994).

R. Muthupillai, D. Lomas, P. Rossman et al., "Magnetic resonance elastography by direct visualization of propagating acoustic strain waves," Science, 269(5232), 1854-1857 (1995).

J. Schmitt, "OCT elastography: imaging microscopic deformation and strain of tissue," Opt Express, 3(6), 199-211 (1998).

X. Liang, V. Crecea, and S. A. Boppart, "Dynamic Optical Coherence Elastography: A Review," J Innov Opt Health Sci, 3(4), 221-233 (2010).

B. F. Kennedy, K. M. Kennedy, and D. D. Sampson, "A Review of Optical Coherence Elastography: Fundamentals, Techniques and Prospects," Ieee Journal of Selected Topics in Quantum Electronics, 20(2), (2014).

H. J. Ko, W. Tan, R. Stack et al., "Optical coherence elastography of engineered and developing tissue," Tissue Eng, 12(1), 63-73 (2006).

B. F. Kennedy, X. Liang, S. G. Adie et al., "In vivo three-dimensional optical coherence elastography," Opt Express, 19(7), 6623-34 (2011).

J. Rogowska, N. Patel, J. Fujimoto et al., "Optical coherence tomographic elastography technique for measuring deformation and strain of atherosclerotic tissues," Heart, 90(5), 556-562 (2004).

C. H. Liu, M. N. Skryabina, J. Li et al., "Measurement of the temperature dependence of Young's modulus of cartilage by phase-sensitive optical coherence elastography," Quantum Electronics, 44(8), 751 (2014).

R. Manapuram, S. Baranov, V. Manne et al., "Assessment of wave propagation on surfaces of crystalline lens with phase sensitive optical coherence tomography," Laser Physics Letters, 8(2), 164 (2011).

J. Li, S. Wang, M. Singh et al., "Air-pulse OCE for assessment of age-related changes in mouse cornea in vivo," Laser Physics Letters, 11(065601), 1612-202X (2014).

J. Kablik, G. D. Monheit, L. Yu et al., "Comparative physical properties of hyaluronic acid dermal fillers," Dermatologic Surgery, 35(s1), 302-312 (2009).

H. Sundaram, B. Voigts, K. Beer et al., "Comparison of the rheological properties of viscosity and elasticity in two categories of soft tissue fillers: calcium hydroxylapatite and hyaluronic acid," Dermatologic Surgery, 36(s3), 1859-1865 (2010).

D. Stocks, H. Sundaram, J. Michaels et al., "Rheological evaluation of the physical properties of hyaluronic acid dermal fillers," Journal of drugs in dermatology: JDD, 10(9), 974-980 (2011).

S. Wang, K. Larin, J. Li et al., "A focused air-pulse system for optical-coherence-tomography-based measurements of tissue elasticity," Laser Physics Letters, 10(7), 075605 (2013).

S. Wang, S. Aglyamov, A. Karpiouk et al., "Assessing the mechanical properties of tissue-mimicking phantoms at different depths as an approach to measure biomechanical gradient of crystalline lens," Biomedical Optics Express, 4(12), 2769-2780 (2013).

S. R. Aglyamov, A. R. Skovoroda, H. Xie et al., "Model-based reconstructive elasticity imaging using ultrasound," International journal of biomedical imaging, 2007, (2007).

U. Sharma, E. W. Chang, and S. H. Yun, "Long-wavelength optical coherence tomography at 1.7 μm for enhanced imaging depth," Optics express, 16(24), 19712-19723 (2008).

R. K. Wang, X. Xu, V. V. Tuchin et al., "Concurrent enhancement of imaging depth and contrast for optical coherence tomography by hyperosmotic agents," JOSA B, 18(7), 948-953 (2001).

X. Liang, and S. A. Boppart, "Biomechanical properties of in vivo human skin from dynamic optical coherence elastography," Biomedical Engineering, IEEE Transactions on, 57(4), 953-959 (2010).

H. Khatam, Q. Liu, and K. Ravi-Chandar, "Dynamic tensile characterization of pig skin," Acta Mechanica Sinica, 30(2), 125-132 (2014).

M. C. Pierce, J. Strasswimmer, B. H. Park, B. Cense, J. F. de Boer, "Advances in optical coherence tomography imaging for dermatology," Journal of Investigative Dermatology, 123(3), 148 (2004).

T. Gambichler, G. Moussa, M. Sand, D. Sand, P. Altmeyer, K. Hoffman, "Applications of optical coherence tomography in dermatology," Journal of Dermatological Science, 40(2), 85 (2005).

E. Sattler, R. Kastle, J. Welzel. "Optical coherence tomography in dermatology" Journal of Biomedical Optics, 18(6), 061224 (2013).

J. Olsen, L. Themstrup, G. B. Jemec, "Optical coherence tomography in dermatology," Giornale Italiano di Dermatologia e Venereologia, (2015).

S. H. Syed, A. J. Coughlin, M. D. Garcia, et al., "Optical coherence tomography guided microinjections in live mouse embryos: high-resolution targeted manipulation for mouse embryonic research," Journal of Biomedical Optics, 20(5), 051020 (2015).

What is claimed is:

1. A method for quantifying effects of a treatment on elasticity of skin in an area of skin, comprising the steps of:
performing a treatment on an area of skin, wherein the treatment produces a zone of skin manipulation within the area of skin, and wherein the treatment comprises an injection of a dermal filler, cross-linking of an injected dermal filler, application of a cream or lotion, or resurfacing;
using a single focused air pulse to stimulate a localized micrometer scale displacement of the skin at a single location within the zone of skin manipulation;
using an optical coherence elastography (OCE) system to measure a temporal displacement profile resulting from the localized micrometer scale displacement of the skin at the single location within the zone of skin manipulation, wherein the temporal displacement profile shows amount of displacement of the skin measured relative to time at the single location;
quantifying biomechanical properties at the single location within the zone of skin manipulation based on an analysis of the temporal displacement profile; and
mapping one or more biomechanical properties to the single location within the zone of skin manipulation to quantify the effects of the treatment on the elasticity of the skin in the area of skin.

2. The method of claim 1, wherein the step of quantifying biomechanical properties comprises quantifying one or more of axial displacement, relaxation rate, relaxation process, frequency of the relaxation process, Young's modulus, elasticity, and viscosity.

3. The method of claim 1, wherein the treatment is an injection of a dermal filler or cross-linking of an injected dermal filler.

4. The method of claim 3, further comprising the step of visualizing changes in the area of skin and in the dermal filler as the injection or the cross-linking is occurring using an optical coherence tomography (OCT) system.

5. The method of claim 3, further comprising a step of using an additional single focused air pulse to stimulate an additional localized micrometer scale displacement of the skin at a single location outside the zone of skin manipulation, wherein the single location outside the zone of skin manipulation lacks an injected dermal filler.

6. The method of claim 3, further comprising a step of using an additional single focused air pulse to stimulate an additional localized micrometer scale displacement of the skin at a single location outside the zone of skin manipulation, wherein the single location outside the zone of skin manipulation lacks a cross-linked dermal filler.

7. A method for quantifying effects of a treatment on elasticity of skin in a target area of skin before and after the treatment, comprising the steps of:
using a single focused air pulse to stimulate a localized micrometer scale displacement of the skin at a single location on the target area of skin before performing a treatment on the target area of skin;
using an optical coherence elastography (OCE) system to measure a temporal displacement profile resulting from the localized micrometer scale displacement of the skin at the single location on the target area of skin wherein the temporal displacement profile shows amount of displacement of the skin measured relative to time at the single location;
quantifying biomechanical properties at the single location on the target area of skin based on an analysis of the temporal displacement profile;
performing a treatment on at least one area of skin within the target area of skin, wherein the treatment produces a zone of skin manipulation within the target area of skin, and wherein the treatment comprises an injection of a dermal filler, cross-linking of an injected dermal filler, application of a cream or lotion, or resurfacing;
using an additional single focused air pulse to stimulate an additional localized micrometer scale displacement of the skin at an additional single location within the zone of skin manipulation;
using an optical coherence elastography (OCE) system to measure an additional temporal displacement profile resulting from the additional localized micrometer scale displacement of the skin at the additional single location within the zone of skin manipulation, wherein the additional temporal displacement profile shows amount of displacement of the skin measured relative to time at the additional single location;
quantifying and comparing biomechanical properties at the additional single location within the zone of skin manipulation based on an analysis of the temporal displacement profile at the single location before the treatment was applied to the area of skin and an analysis of the additional temporal displacement profile at the additional single location within the zone of skin manipulation after the treatment was applied to the area of skin; and
mapping one or more biomechanical properties of the additional single location within the zone of skin manipulation to quantify effects of the treatment on the elasticity of the skin in the area of skin.

8. The method of claim 7, wherein the step of performing a treatment on at least one area of skin comprises an injection of a dermal filler into the at least one area of skin.

9. The method of claim 7, wherein the step of performing a treatment on at least one area of skin comprises cross-linking of an injected dermal filler present in the at least one area of skin.

* * * * *

UNITED STATES PATENT AND TRADEMARK OFFICE
CERTIFICATE OF CORRECTION

PATENT NO. : 11,839,483 B2
APPLICATION NO. : 15/748372
DATED : December 12, 2023
INVENTOR(S) : Kirill Larin et al.

It is certified that error appears in the above-identified patent and that said Letters Patent is hereby corrected as shown below:

In the Specification
1. In Column 6, Line 67, delete "1300 nm," and insert -- ~1300 nm, --, therefor.

In the Claims
2. In Column 14, Line 8, in Claim 7, delete "skin" and insert -- skin, --, therefor.

Signed and Sealed this
Twenty-eighth Day of May, 2024

*Katherine Kelly Vidal*

Katherine Kelly Vidal
*Director of the United States Patent and Trademark Office*